United States Patent
Marash

(10) Patent No.: US 10,549,118 B2
(45) Date of Patent: Feb. 4, 2020

(54) IRRADIATION TREATMENT PLAN SYSTEM AND METHOD

(71) Applicant: P-CURE, LTD., Lod (IL)

(72) Inventor: Michael Marash, Rishon Le'tzion (IL)

(73) Assignee: P-Cure, Ltd., Shilat (IL)

( * ) Notice: Subject to any disclaimer, the term of this patent is extended or adjusted under 35 U.S.C. 154(b) by 211 days.

(21) Appl. No.: 15/744,804

(22) PCT Filed: Jul. 22, 2016

(86) PCT No.: PCT/IL2016/050802
§ 371 (c)(1),
(2) Date: Jan. 14, 2018

(87) PCT Pub. No.: WO2017/013662
PCT Pub. Date: Jan. 26, 2017

(65) Prior Publication Data
US 2019/0009107 A1    Jan. 10, 2019

Related U.S. Application Data

(60) Provisional application No. 62/195,302, filed on Jul. 22, 2015, provisional application No. 62/200,038, filed on Aug. 2, 2015.

(51) Int. Cl.
*A61N 5/10* (2006.01)
*A61N 5/01* (2006.01)

(52) U.S. Cl.
CPC .............. *A61N 5/103* (2013.01); *A61N 5/01* (2013.01); *A61N 5/1049* (2013.01); *A61N 5/1069* (2013.01); *A61N 5/1081* (2013.01)

(58) Field of Classification Search
CPC .... A61N 5/103; A61N 5/1081; A61N 5/1069; A61N 5/01; A61N 5/1049
See application file for complete search history.

(56) References Cited

U.S. PATENT DOCUMENTS

| 7,668,292 B1 * | 2/2010 | Bose | G06F 19/3481 378/65 |
| 7,847,275 B2 * | 12/2010 | Lifshitz | A61B 6/032 250/491.1 |

(Continued)

OTHER PUBLICATIONS

International Search Report dated Jan. 5, 2017 by the USPTO for PCT/IL2016/050802.

(Continued)

*Primary Examiner* — David P Porta
*Assistant Examiner* — Djura Malevic
(74) *Attorney, Agent, or Firm* — Chanoch Kahn; Simon Kahn

(57) ABSTRACT

An irradiation treatment planning method constituted of: controlling a patient support member to rotate about a first axis by an initial rotation angle; imaging the patient; receiving treatment prescriptions; and responsive to the patient image, the treatment prescriptions and allowable ranges of rotation about at least two orthogonal axes, determining an irradiation treatment plan, wherein in the event that the irradiation treatment plan does not meet the treatment prescriptions, the method further comprises: responsive to the patient image, the treatment prescriptions and the allowable rotation ranges, determining rotation angles of the patient support member about the first axis; for each rotation angle, controlling the patient support member to rotate about the first axis by the rotation angle and imaging the patient; and for each rotation angle, determining an irradiation treatment plan portion responsive to the patient image, the treatment prescriptions and the allowable rotation ranges.

20 Claims, 2 Drawing Sheets

(56) References Cited

U.S. PATENT DOCUMENTS

| | | | | |
|---|---|---|---|---|
| 8,121,252 B2* | 2/2012 | Nord | ............ | A61N 5/103 |
| | | | | 378/65 |
| 8,175,892 B2* | 5/2012 | Kapoor | ............ | A61N 5/1048 |
| | | | | 705/2 |
| 8,755,489 B2* | 6/2014 | Lavi | ............ | A61N 5/103 |
| | | | | 378/207 |
| 9,220,919 B2* | 12/2015 | Masumoto | ............ | A61N 5/1037 |
| 9,675,818 B2* | 6/2017 | Hirai | ............ | A61N 5/103 |
| 2005/0228255 A1* | 10/2005 | Saracen | ............ | A61B 6/0457 |
| | | | | 600/407 |
| 2005/0234327 A1* | 10/2005 | Saracen | ............ | A61B 6/0457 |
| | | | | 600/407 |
| 2008/0317216 A1* | 12/2008 | Lifshitz | ............ | A61B 6/032 |
| | | | | 378/209 |
| 2009/0154645 A1* | 6/2009 | Lifshitz | ............ | A61B 6/032 |
| | | | | 378/65 |
| 2012/0123183 A1* | 5/2012 | Lavi | ............ | A61N 5/103 |
| | | | | 600/1 |
| 2013/0178690 A1* | 7/2013 | Masumoto | ............ | A61N 5/1037 |
| | | | | 600/1 |
| 2018/0220975 A1* | 8/2018 | Marash | ............ | A61B 6/032 |

OTHER PUBLICATIONS

Written Opinion of the International Searching Authority dated Jan. 5, 2017 by the USPTO for PCT/IL2016/050802.

* cited by examiner

IRRADIATION TREATMENT PLAN SYSTEM AND METHOD

CROSS-REFERENCE TO RELATED APPLICATIONS

This application claims priority from: U.S. provisional patent application Ser. No. 62/195,302, filed Jul. 22, 2015 and entitled "PATIENT IRRADIATION TREATMENT PLAN IMAGE ADJUSTMENT SYSTEM AND METHOD; and U.S. provisional patent application Ser. 62/200,038, filed Aug. 2, 2015 and entitled "IMAGING SYSTEM AND METHOD", the entire contents of each of with are incorporated herein by reference.

TECHNICAL FIELD

The invention relates generally to the field of teletherapy and in particular to a patient irradiation treatment plan image adjustment system and method.

BACKGROUND OF THE INVENTION

Teletherapy is defined as a treatment methodology in which an irradiation source is at a distance from the body to be treated. X-rays and electron beams have long been used in teletherapy to treat various cancers. Unfortunately, X-rays exhibit a linear energy transfer approaching an exponential attenuation function, and are therefore of minimal safe use for deeply embedded growths. The use of heavy particles, particularly hadrons and more particularly protons, in teletherapy has found increasing acceptance, due to the ability of heavy particles to penetrate to a specific depth without appreciably harming intervening tissue. In particular, the linear energy transfer of hadrons exhibits an inversed depth profile with a marked Bragg peak defined as the point at which the hadrons deposit most of their energy, and occurs at the end of the hadrons path. As a result of this effect, increased energy can be directed at an embedded growth as compared to X-rays and electron beams, which particularly harm intervening tissues. While the term hadrons include a wide range of particles, practically, protons and various ions are most widely used in therapy. For clarity, this document will describe treatment as being accomplished with protons, however this is not meant to be limiting in any way.

The protons or ions can be focused to a target volume of variable penetration depth. In this way the dose profile can be matched closely to the target volume with a high precision. In order to ensure complete irradiation of the target growth, a plurality of beams arriving at the embedded growth from several different directions is preferred. The point at which the plurality of beams intersects, whether they are beamed sequentially or simultaneously, is termed the isocenter, and to maximize biological effectiveness the isocenter must be precisely collocated with the target growth.

Irradiation treatment is performed on a target tissue in a well defined process. In a first stage, known as the treatment planning stage, the target tissue is imaged and a treatment plan comprising dosage, patient position, and irradiation angles are defined. Furthermore, placement markers are defined, so as to ensure that subsequent irradiation sessions are properly targeted. Irradiation is then performed, responsive to the developed treatment plan, at a plurality of treatment sessions over a period of time, each session being known as a fraction. At each such fraction, care must be taken to ensure proper patient positioning, responsive to the placement markers, so as to avoid damage to organs in vicinity of the target tissue. Positioning of the patient responsive to the markers is performed based on visualization of the patient, responsive to the defined markers.

Particularly, during each fraction, the patient is positioned on a patient support member, such as a bed, in a setup position. The setup position is identical to the patient position during the imaging of the treatment planning stage, except that is in the treatment room and the center of the growth mass is positioned at the isocenter of the irradiation source. The setup position of the patient is optionally verified by imaging and/or positioning devices. Unfortunately, current irradiation systems are set up such that the setup position of the patient is always perpendicular to the central axis of the irradiation beam nozzle of the irradiation source. This limits the possibilities for patient positioning for better comfort or other constraints of the treatment room, especially when the irradiation source has a fixed position and is not moveable.

SUMMARY OF THE INVENTION

Accordingly, it is a principal object of the present invention to overcome disadvantages of prior art methods and arrangements of teletherapy. This is provided in the present invention by an irradiation treatment plan system comprising: a patient support member arranged to support a patient, the patient support member arranged to be rotated about three orthogonal axes; an imager; a memory, the memory having stored thereon, for at least two of the three orthogonal axes, information regarding the allowable range of rotation of the patient support member about the respective axis; and a control circuitry, the control circuitry arranged to: control the patient support member to rotate about a first of the three orthogonal axes by a predetermined initial rotation angle; subsequent to the rotation about the first axis, control the imager to image the patient; receive information regarding treatment prescriptions of the patient; and responsive to the patient image, the received treatment prescription information and the allowable rotation range information, determine a first irradiation treatment plan, wherein the control circuitry is further arranged, in the event that the determined first irradiation treatment plan meets the patient treatment prescriptions, to output the determined first irradiation treatment plan, and wherein the control circuitry is further arranged, in the event that the determined first irradiation treatment plan does not meet the patient treatment prescriptions, to: responsive to the patient image, the received treatment prescription information and the allowable rotation range information, determine a plurality of rotation angles of the patient support member about the first axis; for each of the plurality of determined rotation angles, different than the predetermined initial rotation angle, control the patient support member to rotate about the first axis by the respective determined rotation angle and control the imager to image the patient; for each of the plurality of determined rotation angles, determine an irradiation treatment plan portion responsive to the respective patient image, the patient treatment prescriptions and the allowable rotation range information; and output each of the plurality of determined treatment plan portions.

In one embodiment, the control circuitry is further arranged, responsive to the patient image at the predetermined initial rotation angle and the received treatment prescription information, to determine a second irradiation treatment plan, the second irradiation treatment plan determined without the limits of the allowable rotation range information, wherein the determination of the plurality of rotation angles is responsive to the determined second irradiation treatment plan. In another embodiment, the allowable range of rotation of the patient support member about the first axis is in relation to a coordinate system centered on the patient and the allowable range of rotation of the patient support member about the second axis is in relation to a coordinate system centered on a room containing the patient support member, wherein the control circuitry is further arranged to map the allowable range of rotation about the second axis to the patient centered coordinate system, the first irradiation treatment plan determination responsive to the outcome of the mapping.

In one embodiment, the control circuitry is further arranged, in the event that the determined first irradiation treatment plan does not meet the patient treatment prescriptions, to: adjust the allowable range of rotation of the patient support member about at least one of the plurality of three axes; and responsive to the adjusted at least one allowable range, determine an additional first irradiation treatment plan, the arrangement to determine a plurality of rotation angles performed only in the event that the determined additional first irradiation does not meet the patient treatment prescriptions. In one further embodiment, the adjustment of the allowable range of rotation about at least one of the plurality of three axes comprises an adjustment of the allowable range of rotation about two of the plurality of three axes.

In one embodiment, the memory has stored thereon information regarding the allowable range of rotation of the patient support member about all of the three orthogonal axes. In another embodiment, the imager is a computed tomography (CT) imager.

In one independent embodiment, an irradiation treatment planning method for a patient supported by a patient support member which is arranged to be rotated about three orthogonal axes is provided, the method comprising: rotating the patient support member about a first of the three orthogonal axes by a predetermined initial rotation angle; subsequent to the rotation about the first axis, imaging the patient; receiving information regarding treatment prescriptions of the patient; and responsive to the patient image, the received treatment prescription information and information regarding an allowable range of rotation of the patient support member about at least two of the three orthogonal axes, determining a first irradiation treatment plan, wherein in the event that the determined first irradiation treatment plan meets the patient treatment prescriptions, the method further comprises outputting the determined first irradiation treatment plan, and wherein in the event that the determined first irradiation treatment plan does not meet the patient treatment prescriptions, the method further comprises: responsive to the patient image, the received treatment prescription information and the allowable rotation range information, determining a plurality of rotation angles of the patient support member about the first axis; for each of the plurality of determined rotation angles which is different than the predetermined initial rotation angle, rotating the patient support member about the first axis by the respective determined rotation angle and imaging the patient; for each of the plurality of determined rotation angles, determining an irradiation treatment plan portion responsive to the respective patient image, the patient treatment prescriptions and the allowable rotation range information; and outputting each of the plurality of determined treatment plan portions.

In one embodiment, the method further comprises, responsive to the patient image at the predetermined initial rotation angle and the received treatment prescription information, determining a second irradiation treatment plan, the second irradiation treatment plan determined without the limits of the allowable rotation range information, wherein the determination of the plurality of rotation angles is responsive to the determined second irradiation treatment plan. In another embodiment, the allowable range of rotation of the patient support member about the first axis is in relation to a coordinate system centered on the patient and the allowable range of rotation of the patient support member about the second axis is in relation to a coordinate system centered on a room containing the patient support member, and wherein the method further comprises mapping the allowable range of rotation about the second axis to the patient centered coordinate system, the first irradiation treatment plan determination responsive to the outcome of the mapping.

In one embodiment, the method further comprises in the event that the determined first irradiation treatment plan does not meet the patient treatment prescriptions: adjusting the allowable range of rotation of the patient support member about at least one of the plurality of three axes; and responsive to the adjusted at least one allowable range, determining an additional first irradiation treatment plan, the arrangement to determine a plurality of rotation angles performed only in the event that the determined additional first irradiation does not meet the patient treatment prescriptions. In one further embodiment, the adjustment of the allowable range of rotation about at least one of the plurality of three axes comprises an adjustment of the allowable range of rotation about two of the plurality of three axes.

In one embodiment, the information regarding the allowable range of rotation of the patient support member comprises information regarding the allowable range of rotation of the patient support member about all of the three orthogonal axes. In another embodiment, the imaging comprises computed tomography (CT) imaging.

In another independent embodiment, an irradiation treatment plan system is provided, the system comprising: a patient support member arranged to support a patient, the patient support member arranged to be rotated about three orthogonal axes, the patient support member initially rotated about a first of the three axes by a predetermined initial rotation angle; an imager; a memory, the memory having stored thereon, for at least two of the three orthogonal axes, information regarding the allowable range of rotation of the patient support member about the respective axis; and a control circuitry, the control circuitry arranged to: control the imager to image the patient; receive information regarding treatment prescriptions of the patient; and responsive to the patient image, the received treatment prescription information and the allowable rotation range information, determine a first irradiation treatment plan, wherein the control circuitry is further arranged, in the event that the determined first irradiation treatment plan meets the patient treatment prescriptions, to output the determined first irradiation treatment plan, and wherein the control circuitry is further arranged, in the event that the determined first irradiation treatment plan does not meet the patient treatment prescriptions, to: responsive to the patient image, the received treatment prescription information and the allowable rotation range information, determine a plurality of rotation angles of the patient support member about the first axis; for each of the plurality of determined rotation angles which is different than the predetermined initial rotation angle, control the patient support member to rotate about the first axis by the respective determined rotation angle and control the imager to image the patient; for each of the plurality of determined rotation angles, determine an irradiation treatment plan portion responsive to the respective patient image, the patient treatment prescriptions and the allowable rotation range information; and output each of the plurality of determined treatment plan portions.

In one embodiment, the control circuitry is further arranged, responsive to the patient image at the predetermined initial rotation angle and the received treatment prescription information, to determine a second irradiation treatment plan, the second irradiation treatment plan determined without the limits of the allowable rotation range information, wherein the determination of the plurality of rotation angles is responsive to the determined second irradiation treatment plan. In another embodiment, the allowable range of rotation of the patient support member about the first axis is in relation to a coordinate system centered on the patient and the allowable range of rotation of the patient support member about the second axis is in relation to a coordinate system centered on a room containing the patient support member, and wherein the control circuitry is further arranged to map the allowable range of rotation about the second axis to the patient centered coordinate system, the first irradiation treatment plan determination responsive to the outcome of the mapping.

In one embodiment, the control circuitry is further arranged, in the event that the determined first irradiation treatment plan does not meet the patient treatment prescriptions, to: adjust the allowable range of rotation of the patient support member about at least one of the plurality of three axes; and responsive to the adjusted at least one allowable range, determine an additional first irradiation treatment plan, the arrangement to determine a plurality of rotation angles performed only in the event that the determined additional first irradiation does not meet the patient treatment prescriptions. In one further embodiment, the adjustment of the allowable range of rotation about at least one of the plurality of three axes comprises an adjustment of the allowable range of rotation about two of the plurality of three axes.

In one embodiment, the memory has stored thereon information regarding the allowable range of rotation of the patient support member about all of the three orthogonal axes.

Additional features and advantages of the invention will become apparent from the following drawings and description.

BRIEF DESCRIPTION OF THE DRAWINGS

For a better understanding of the invention and to show how the same may be carried into effect, reference will now be made, purely by way of example, to the accompanying drawings in which like numerals designate corresponding elements or sections throughout.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the accompanying drawings:

FIGS. 1A-1C illustrate a high level schematic diagram of an irradiation treatment plan system, according to certain embodiments; and FIG. 2 illustrates a high level flow chart of an irradiation treatment planning method, according to certain embodiments.

DETAILED DESCRIPTION OF THE PREFERRED EMBODIMENTS

Figure 1A:
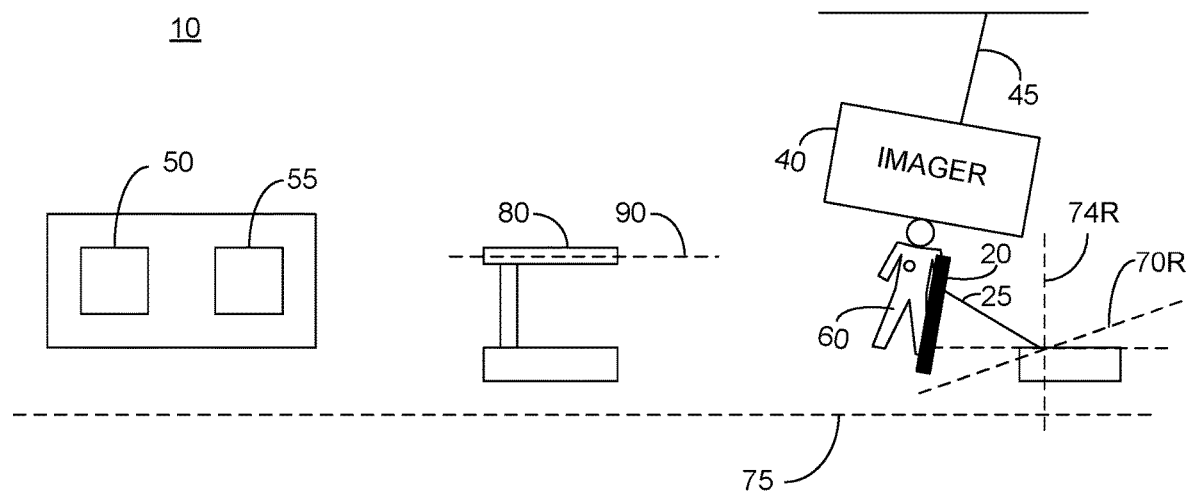

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Figure 1B:
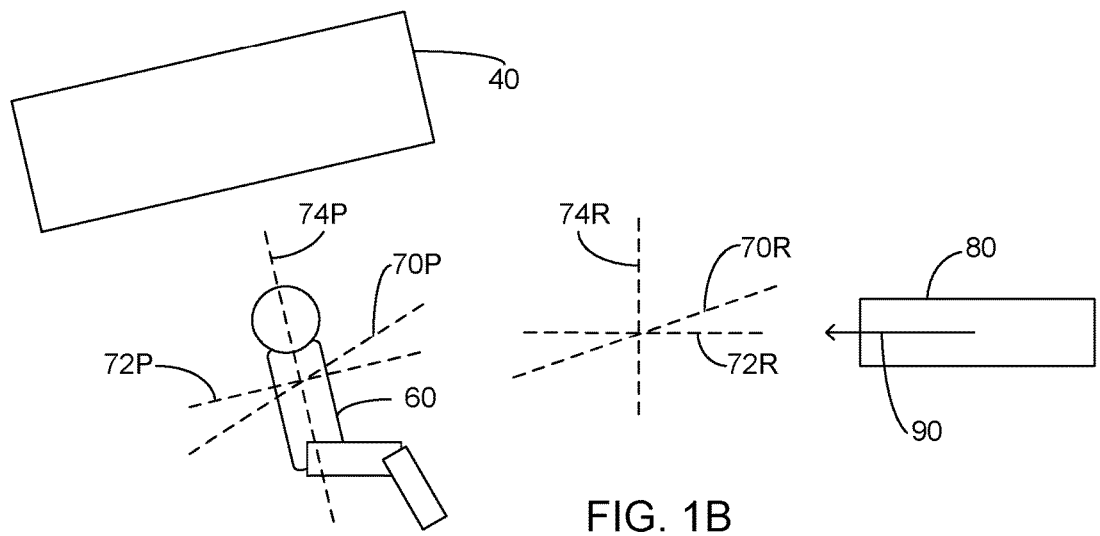
Figure 1C:
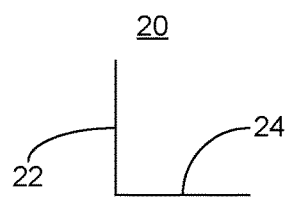

FIG. 1A illustrates a high level schematic diagram of an irradiation treatment plan system 10, according to certain embodiments. Irradiation treatment plan system 10 comprises: a patient support member 20; an imager 40, optionally comprising a computed tomography (CT) imager; an imager rotation mechanism 45; and a control unit comprising a control circuitry 50 and a memory 55. In one preferred embodiment, patient support member 20 comprises a chair such that a patient 60 supported by patient support member 20 is in a sitting position supported by a back rest 22 and a seat 24, as illustrated in FIG. 1C. In one further embodiment, patient support member 20 can be converted to a horizontal bed such that a patient 60 supported by patient support member 20 is lying down. Patient support member 20 further comprises a rotation mechanism 25. Rotation mechanism 25 is arranged to rotate patient support member 20 about three orthogonal axes 70R, 72R and 74R. Specifically, axis 70R is parallel to a floor 75 of the treatment room comprising irradiation treatment plan system 10. Axis 72R is parallel to floor 75 and orthogonal to axis 70R. Axis 74R is orthogonal to floor 75. The rotation of patient support member 20 causes a rotation of patient 60 about three orthogonal axes 70P, 72P and 74P. Specifically, axis 70P is orthogonal to a longitudinal axis of back rest 22 of patient support member 20 and orthogonal to a longitudinal axis of seat 24 of patient support member 20 such that a negative rotation of patient support member 20 about axis 70P will cause patient 60 to lay back, as illustrated in FIG. 1B. Axis 72P is parallel to the longitudinal axis of seat 24 of patient support member 20 such that a rotation about axis 72P will cause patient 60 to tip sideways. Axis 74P is parallel to the longitudinal axis of back rest 22 of patient support member 20 such that a rotation about axis 74P will cause patient 60 to swivel. In one embodiment, axes 70P, 72P and 74P correspond to axes 70R, 72R and 74R, respectively.

Imager rotation mechanism 45 is arranged to rotate imager 40 about axis 70R. In one non-limiting embodiment, imager rotation mechanism 45 is constructed and operated as described in U.S. patent application publication S/N 2015/0208992, published Jul. 30, 2015 to Marash et al., and entitled "APPARATUS AND METHOD FOR PROVIDING PATIENT IMAGING", the entire contents of which are incorporated herein by reference.

Patient support member 20 is positioned in relation to an irradiation source 80. In one embodiment, irradiation source 80 is supported by a gantry which allows movement thereof. In another embodiment, irradiation source 80 is a fixed beam irradiation source and is arranged to output an irradiation beam exhibiting a fixed central axis 90 which corresponds to the central axis of a nozzle of irradiation source 80 (not shown). Particularly, the term 'fixed beam irradiation source', as used herein, is meant that irradiation source 80 has a predetermined fixed position and irradiation angle and the angle of central axis 90 in relation to floor 75 and walls of the treatment room containing irradiation source 80 is not adjusted for patient 60. In one embodiment, the irradiation beam output by irradiation source 80 is constituted primarily of hadrons, preferably protons. In one non-limiting embodiment, control circuitry 50 is one of a processor and an ASIC circuitry. Control circuitry 50 is in communication with patient support member 20 and imager 40 (connections not shown). In one embodiment (not shown) two imagers 40 are provided, optionally one imager 40 arranged to image patient 60 at a plurality of angles and the other imager 40 arranged to image patient 60 in a horizontal position. In another embodiment (not shown), imager 40, or imagers 40, are in a different room than irradiation source 80.

Memory 55 has stored thereon information regarding the allowable range of rotation of patient 60 about axes 70P and 72P. In another embodiment, memory 55 has stored thereon information regarding the allowable range of rotation of patient 60 about axes 70P, 72P and 74P. In another embodiment, memory 55 has stored thereon information regarding the allowable range of rotation of patient 60 about axis 70P, the allowable range of rotation of patient support member 20 about axis 72R and, optionally, the allowable range of rotation of patient support member 20 about axis 74R. Memory 55 further has stored thereon information regarding the relationship between axes 70R, 72R and 74R and axes 70P, 72P and 74P. In one embodiment, the allowable range of rotation about axis 70P is a 30 degree range, from −5 degrees to −35 degrees, a negative angle meaning that patient 60 is laid backwards. In another embodiment, the allowable range of rotation about axis 72R is a 20 degree range, 10 degrees in each direction. In another embodiment, the allowable range of rotation about axis 74R is 360 degrees. The allowable ranges represent the desired limits of rotation of patient 60 during treatment to avoid uncomfortable positions, mechanical limitations of patient support member 20 and/or limitations due to the position of central axis 90 of irradiation source 80.

In operation, patient 60 is supported by patient support member 20. Control circuitry 50 is arranged to control rotation mechanism 25 of patient support member 20 such that patient 60 is rotated about axis 70P by a predetermined initial rotation angle. Optionally, the predetermined initial rotation angle is −20 degrees, i.e. patient 60 is laid back by 20 degrees. In another embodiment, patient support member 20 is already rotated about axis 70P by the predetermined initial rotation angle. Subsequent to the rotation about axis 70P, control circuitry 50 is arranged to control imaging rotation mechanism 45 of imager 40 to rotate imager 40 about axis 70R such that imager 40 is aligned with patient 60 and is further arranged to control imager 40 to image patient 60. Imager 40 is arranged to output the image, or images, of patient 60 to control circuitry 50.

Control circuitry 50 is arranged to receive from a user input console, or from an external network, treatment prescriptions for the treatment of patient 60. In one embodiment, the treatment prescriptions include the minimum dose amount to be applied to the target tissue and the maximum dose amount to be applied to surrounding critical structures, e.g. at least 90% of the dose to the target tissue and less than 10% of the dose to the critical structures.

Responsive to the images of patient 60 received from imager 40, the received treatment prescriptions and the allowable rotation range information stored on memory 55, control circuitry 50 is arranged to determine a first irradiation treatment plan for patient 60. In one embodiment, prior to the treatment planning, control circuitry 50 is arranged to instruct the treatment planning software to rotate the irradiation beam of the treatment plan by the initial rotation angle of patient 60. Alternatively, control circuitry 50 is arranged to rotate the received image, or images, by the initial rotation angle of patient 60. In another embodiment, prior to the treatment planning, control circuitry 50 is arranged to map the rotation limitations about axes 72R and 74R to the coordinate system of axes 70P, 72P and 74P, since the treatment plan is calculated in relation to the coordinate system of patient 60.

In one embodiment, the nodes of a 3 dimensional (3D) grid of the image are each rotated about the respective one of axes 72P and 74P which corresponds with axes 72R and 74R, respectively. After the rotation, each grid node will be in its local 3D cell, which is defined by eight nodes of the 3D grid before the rotation. The HU-value of the node is calculated by interpolation of the corresponding HU-values at the nodes of the local cell.

In one embodiment, control circuitry 50 is further arranged to determine a second irradiation treatment plan for patient 60, the second irradiation treatment plan computed without the rotation range limitations used to compute the first irradiation treatment plan. Control circuitry 50 is arranged to determine whether the first irradiation treatment plan is able to meet the treatment prescriptions while maintaining the rotation range limitations. In one embodiment, control circuitry 50 is arranged to compare the first and second irradiation treatment plans, and determine whether the treatment prescriptions are met responsive to the outcome of the treatment plan comparison. In the event that the first irradiation treatment plan meets the patient treatment prescriptions, control circuitry 50 is arranged to output the determined first irradiation treatment plan, optionally to a user console. Further optionally, control circuitry 50 is arranged to control irradiation source 80 to irradiate patient 60 in accordance with the output irradiation treatment plan. Control circuitry 50 is further arranged, prior to the output of the first irradiation treatment plan to map the planned rotation angles of patient 60 about axes 72P and 74P to the coordination system of axes 70R, 72R and 74R.

In the event that control circuitry 50 determines that the first irradiation treatment plan does not meet the patient treatment prescriptions, control circuitry 50 is arranged, responsive to the received patient images, the received treatment prescription information and the allowable rotation range information, to determine a plurality of rotation angles of patient 60 about axis 70P which will allow a plurality of irradiation treatment portions which together will meet the patient treatment prescriptions. Control circuitry 50 is further arranged to determine the corresponding rotation angles of patient support member 20 about axis 70R. In one embodiment, the plurality of rotation angles is responsive to the optionally determined second irradiation treatment plan. One of the plurality of rotation angles can in one embodiment be the predetermined initial rotation angle. The determined rotation angles are limited by the allowable rotation range about axis 70P, however they can in one embodiment include a −90 degree rotation, i.e. a horizontal position.

For each of the plurality of determined rotation angles, not including the predetermined initial rotation angle, control circuitry 50 is arranged to: control patient support member 20 to rotate patient 60 about axis 70P by the respective determined rotation angle; control imager rotation mechanism 45 to rotate imager 40 accordingly; and control imager 40 to image patient 60 at the respective rotation angle. No image is necessary for the initial rotation angle because patient 60 has already been imaged at that angle.

For each of the plurality of determined rotation angles, control circuitry 50 is arranged to determine an irradiation treatment plan portion responsive to the respective images received from imager 40 at the respective rotation angle, the patient treatment prescriptions and the allowable rotation range information for axis 72R and optionally axis 74R. Control circuitry 50 is further arranged to output each of the determined treatment plan portions, as described above in relation to the output first irradiation treatment plan. In one embodiment, in the event that the combination of the determined irradiation treatment plan portions still do not meet the patient treatment prescriptions, control circuitry 50 is arranged to again determine additional rotation angles of patient 60 about axis 70P and determine additional irradiation treatment plan portions.

In one embodiment, when control circuitry 50 has determined that the first irradiation treatment plan does not meet the treatment prescriptions, control circuitry 50 is arranged to adjust the allowable rotation range about axis 72R, and optionally axis 74R, and responsive thereto determine an additional first irradiation treatment plan. Optionally, only in the event that the additional first irradiation treatment plan does not meet the patient treatment prescriptions does control circuitry 50 determine the additional rotation angles for the irradiation treatment portions. Similarly, in the event that the combination of the determined irradiation treatment plan portions do not meet the patient treatment prescriptions control circuitry 50 is arranged to adjust the allowable rotation range of patient 60 about axis 70P and new rotation angles are determined.

Figure 2:
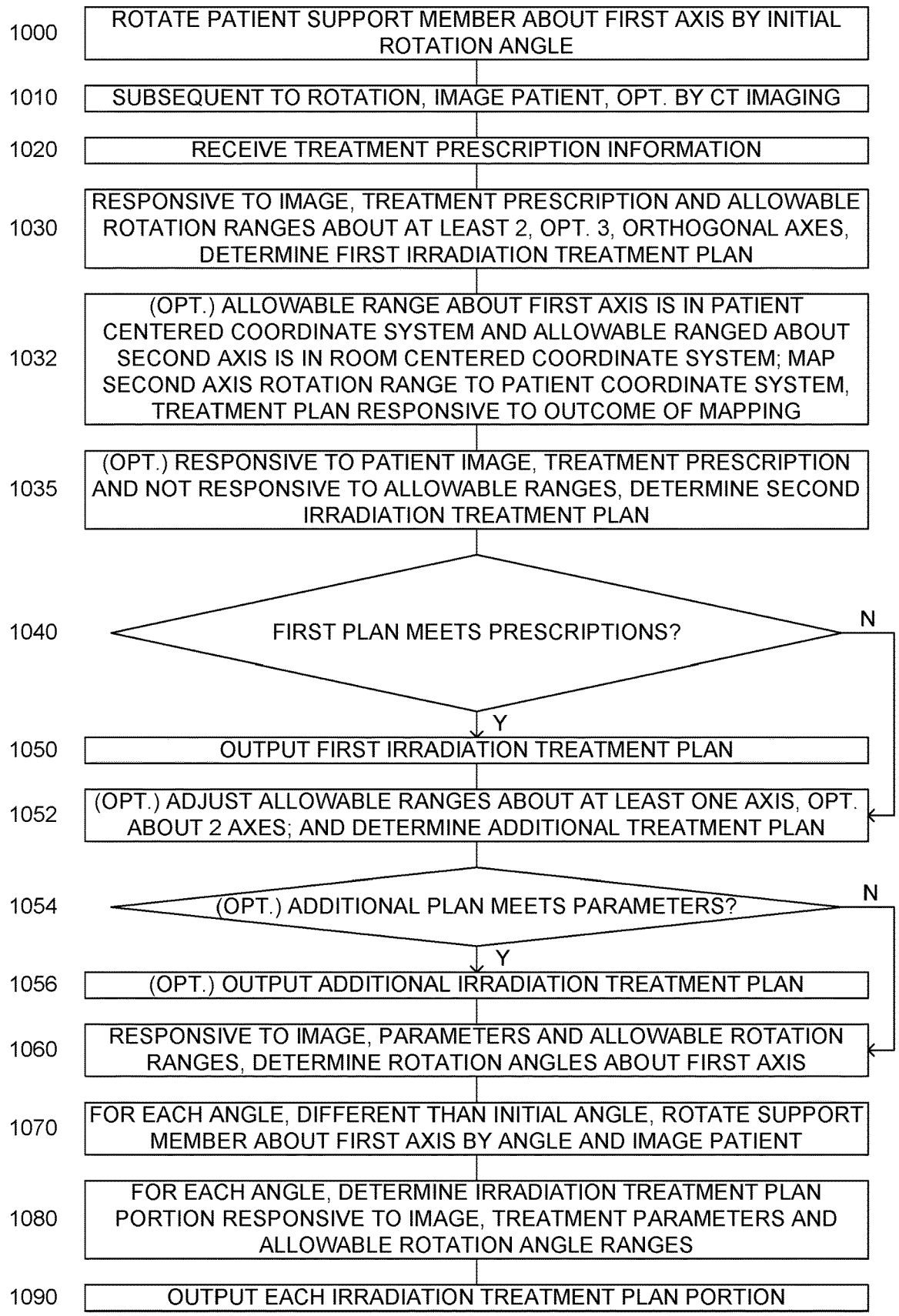

FIG. 2 illustrates a high level flow chart of an irradiation treatment planning method for a patient supported by a patient support member which is arranged to be rotated about three orthogonal axes, according to certain embodiments. In stage 1000, in one embodiment, the patient support member is rotated about a first of the three orthogonal axes by a predetermined initial rotation angle. In another embodiment, the patient support member is arranged to initially be in a rotated position about the first axis by the predetermined initial rotation angle and no additional rotation is necessary during stage 1000. In stage 1010, subsequent to the rotation about the first axis of stage 1000, the patient is imaged, optionally by CT imaging. In stage 1020, information regarding treatment prescriptions of the patient is received. In stage 1030, responsive to the patient image of stage 1010, the received treatment prescription information of stage 1020 and information regarding an allowable range of rotation of the patient support member about at least two of the three orthogonal axes, optionally all three axes, a first irradiation treatment plan is determined.

In optional stage 1032, the allowable range of rotation of the patient support member about the first axis is in relation to a coordinate system centered on the patient and the allowable range of rotation of the patient support member about the second axis is in relation to a coordinate system centered on a room containing the patient support member. The allowable range of rotation about the second axis is mapped to the patient centered coordinate system, the first irradiation treatment plan determination responsive to the outcome of the mapping.

In optional stage 1035, responsive to the patient image at the predetermined initial rotation angle of stage 1010 and the received treatment prescription information of stage 1020, a second irradiation treatment plan is determined, the second irradiation treatment plan determined without the limits of the allowable rotation range information of stage 1030.

In stage 1040, the determined first irradiation treatment plan of stage 1030 is analyzed to determine whether it meets the treatment prescriptions of stage 1020 to determine if they are met, optionally responsive to the second irradiation treatment plan of optional stage 1035. In the event that the determined first irradiation treatment plan meets the patient treatment prescriptions, in stage 1050 the determined first irradiation treatment plan of stage 1030 is output.

In the event that the determined first irradiation treatment plan does not meet the patient treatment prescriptions of stage 1020, in optional stage 1052 the allowable rotation range for at least one of the axes, and optionally 2 of the axes, of stage 1030 are adjusted. Responsive to the adjustment, an additional first treatment plan is determined. In optional stage 1054, the additional first treatment plan of optional stage 1052 is analyzed to determine whether it meets the treatment prescriptions of stage 1020. In the event that the additional first treatment plan meets the treatment prescriptions, in optional stage 1056 the additional first treatment plan is output.

In the event that the additional first treatment plan of optional stage 1052 does not meet the treatment prescriptions of stage 1020, in stage 1060, responsive to the patient image of stage 1010, the received treatment prescription information and the allowable rotation range information of stage 1030, a plurality of rotation angles of the patient support member about the first axis are determined. In stage 1070, for each of the plurality of determined rotation angles of stage 1060 which is different than the predetermined initial rotation angle of stage 1000, the patient support member is controlled to rotate about the first axis by the respective determined rotation angle and the patient is imaged.

In stage 1080, for each of the plurality of determined rotation angles of stage 1060, an irradiation treatment plan portion is determined responsive to the respective patient image of stage 1070, the patient treatment prescriptions of stage 1020 and the allowable rotation range information of stage 1030. In stage 1090, each of the plurality of determined treatment plan portions of stage 1080 are output.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

Unless otherwise defined, all technical and scientific terms used herein have the same meanings as are commonly understood by one of ordinary skill in the art to which this invention belongs. Although methods similar or equivalent to those described herein can be used in the practice or testing of the present invention, suitable methods are described herein.

All publications, patent applications, patents, and other references mentioned herein are incorporated by reference in their entirety. In case of conflict, the patent specification, including definitions, will prevail. In addition, the materials, methods, and examples are illustrative only and not intended to be limiting.

The terms "include", "comprise" and "have" and their conjugates as used herein mean "including but not necessarily limited to".

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

The invention claimed is:

1. An irradiation treatment plan system comprising:
    a patient support member arranged to support a patient, said patient support member arranged to be rotated about three orthogonal axes;
    an imager;
    a memory, said memory having stored thereon, for at least two of the three orthogonal axes, information regarding an allowable range of rotation of said patient support member about the respective axis; and
    a control circuitry, said control circuitry arranged to:
        control said patient support member to rotate about a first of the three orthogonal axes by a predetermined initial rotation angle;
        subsequent to said rotation about the first axis, control said imager to image the patient;
        receive information regarding treatment prescriptions of the patient; and
        responsive to said patient image, said received treatment prescription information and said allowable rotation range information, determine a first irradiation treatment plan,
            wherein said control circuitry is further arranged, in the event that said determined first irradiation treatment plan meets the patient treatment prescriptions, to output said determined first irradiation treatment plan, and
            wherein said control circuitry is further arranged, in the event that said determined first irradiation treatment plan does not meet the patient treatment prescriptions, to:
                responsive to said patient image, said received treatment prescription information and said allowable rotation range information, determine a plurality of rotation angles of said patient support member about the first axis;
                for each of said plurality of determined rotation angles which is different than the predetermined initial rotation angle, control said patient support member to rotate about the first axis by said respective determined rotation angle and control said imager to image the patient;
                for each of said plurality of determined rotation angles, determine an irradiation treatment plan portion responsive to said respective patient image, the patient treatment prescriptions and said allowable rotation range information; and
                output each of said plurality of determined treatment plan portions.

2. The system of claim 1, wherein said control circuitry is further arranged, responsive to said patient image at the predetermined initial rotation angle and said received treatment prescription information, to determine a second irradiation treatment plan, said second irradiation treatment plan determined without the limits of said allowable rotation range information,
    wherein said determination of said plurality of rotation angles is responsive to said determined second irradiation treatment plan.

3. The system of claim 1, wherein the allowable range of rotation of said patient support member about the first axis is in relation to a coordinate system centered on the patient and the allowable range of rotation of said patient support member about the second axis is in relation to a coordinate system centered on a room containing said patient support member, and
    wherein said control circuitry is further arranged to map the allowable range of rotation about the second axis to the patient centered coordinate system, said first irradiation treatment plan determination responsive to the outcome of said mapping.

4. The system of claim 1, wherein said control circuitry is further arranged, in the event that said determined first irradiation treatment plan does not meet the patient treatment prescriptions, to:
    adjust the allowable range of rotation of said patient support member about at least one of the plurality of three axes; and
    responsive to said adjusted at least one allowable range, determine an additional first irradiation treatment plan, said arrangement to determine a plurality of rotation angles performed only in the event that said determined additional first irradiation does not meet the patient treatment prescriptions.

5. The system of claim 4, wherein said adjustment of the allowable range of rotation about at least one of the plurality of three axes comprises an adjustment of the allowable range of rotation about two of the plurality of three axes.

6. The system of claim 1, wherein said memory has stored thereon information regarding the allowable range of rotation of said patient support member about all of the three orthogonal axes.

7. The system of claim 1, wherein said imager is a computed tomography (CT) imager.

8. An irradiation treatment planning method for a patient supported by a patient support member which is arranged to be rotated about three orthogonal axes, the method comprising:
    rotating the patient support member about a first of the three orthogonal axes by a predetermined initial rotation angle;
    subsequent to said rotation about the first axis, imaging the patient;
    receiving information regarding treatment prescriptions of the patient; and
    responsive to said patient image, said received treatment prescription information and information regarding an allowable range of rotation of the patient support member about at least two of the three orthogonal axes, determining a first irradiation treatment plan,
        wherein in the event that said determined first irradiation treatment plan meets the patient treatment prescriptions, the method further comprises outputting said determined first irradiation treatment plan, and
        wherein in the event that said determined first irradiation treatment plan does not meet the patient treatment prescriptions, the method further comprises:
            responsive to said patient image, said received treatment prescription information and said allowable rotation range information, determining a plurality of rotation angles of said patient support member about the first axis;

for each of said plurality of determined rotation angles which is different than the predetermined initial rotation angle, rotating said patient support member about the first axis by said respective determined rotation angle and imaging the patient;

for each of said plurality of determined rotation angles, determining an irradiation treatment plan portion responsive to said respective patient image, the patient treatment prescriptions and said allowable rotation range information; and outputting each of said plurality of determined treatment plan portions.

9. The method of claim 8, further comprising, responsive to said patient image at the predetermined initial rotation angle and said received treatment prescription information, determining a second irradiation treatment plan, said second irradiation treatment plan determined without the limits of said allowable rotation range information, wherein said determination of said plurality of rotation angles is responsive to said determined second irradiation treatment plan.

10. The method of claim 8, wherein the allowable range of rotation of the patient support member about the first axis is in relation to a coordinate system centered on the patient and the allowable range of rotation of said patient support member about the second axis is in relation to a coordinate system centered on a room containing said patient support member, and wherein the method further comprises mapping the allowable range of rotation about the second axis to the patient centered coordinate system, said first irradiation treatment plan determination responsive to the outcome of said mapping.

11. The method of claim 8, further comprising, in the event that said determined first irradiation treatment plan does not meet the patient treatment prescriptions:

adjusting the allowable range of rotation of said patient support member about at least one of the plurality of three axes; and responsive to said adjusted at least one allowable range, determining an additional first irradiation treatment plan, said arrangement to determine a plurality of rotation angles performed only in the event that said determined additional first irradiation does not meet the patient treatment prescriptions.

12. The method of claim 11, wherein said adjustment of the allowable range of rotation about at least one of the plurality of three axes comprises an adjustment of the allowable range of rotation about two of the plurality of three axes.

13. The method of claim 8, wherein the information regarding the allowable range of rotation of the patient support member comprises information regarding the allowable range of rotation of the patient support member about all of the three orthogonal axes.

14. The method of claim 8, wherein said imaging comprises computed tomography (CT) imaging.

15. An irradiation treatment plan system comprising:

a patient support member arranged to support a patient, said patient support member arranged to be rotated about three orthogonal axes, said patient support member initially rotated about a first of the three axes by a predetermined initial rotation angle;

an imager;

a memory, said memory having stored thereon, for at least two of the three orthogonal axes, information regarding an allowable range of rotation of said patient support member about the respective axis; and a control circuitry, said control circuitry arranged to:

control said imager to image the patient;

receive information regarding treatment prescriptions of the patient; and responsive to said patient image, said received treatment prescription information and said allowable rotation range information, determine a first irradiation treatment plan, wherein said control circuitry is further arranged, in the event that said determined first irradiation treatment plan meets the patient treatment prescriptions, to output said determined first irradiation treatment plan, and wherein said control circuitry is further arranged, in the event that said determined first irradiation treatment plan does not meet the patient treatment prescriptions, to:

responsive to said patient image, said received treatment prescription information and said allowable rotation range information, determine a plurality of rotation angles of said patient support member about the first axis;

for each of said plurality of determined rotation angles which is different than the predetermined initial rotation angle, control said patient support member to rotate about the first axis by said respective determined rotation angle and control said imager to image the patient;

for each of said plurality of determined rotation angles, determine an irradiation treatment plan portion responsive to said respective patient image, the patient treatment prescriptions and said allowable rotation range information; and output each of said plurality of determined treatment plan portions.

16. The system of claim 15, wherein said control circuitry is further arranged, responsive to said patient image at the predetermined initial rotation angle and said received treatment prescription information, to determine a second irradiation treatment plan, said second irradiation treatment plan determined without the limits of said allowable rotation range information, wherein said determination of said plurality of rotation angles is responsive to said determined second irradiation treatment plan.

17. The system of claim 15, wherein the allowable range of rotation of said patient support member about the first axis is in relation to a coordinate system centered on the patient and the allowable range of rotation of said patient support member about the second axis is in relation to a coordinate system centered on a room containing said patient support member, and wherein said control circuitry is further arranged to map the allowable range of rotation about the second axis to the patient centered coordinate system, said first irradiation treatment plan determination responsive to the outcome of said mapping.

18. The system of claim 15, wherein said control circuitry is further arranged, in the event that said determined first irradiation treatment plan does not meet the patient treatment prescriptions, to:

adjust the allowable range of rotation of said patient support member about at least one of the plurality of three axes; and responsive to said adjusted at least one allowable range, determine an additional first irradiation treatment plan, said arrangement to determine a plurality of rotation angles performed only in the event that said determined additional first irradiation does not meet the patient treatment prescriptions.

19. The system of claim 18, wherein said adjustment of the allowable range of rotation about at least one of the plurality of three axes comprises an adjustment of the allowable range of rotation about two of the plurality of three axes.

20. The system of claim 15, wherein said memory has stored thereon information regarding the allowable range of rotation of said patient support member about all of the three orthogonal axes.

* * * * *